(12) United States Patent
Xu et al.

(10) Patent No.: US 11,447,625 B2
(45) Date of Patent: Sep. 20, 2022

(54) PERCHLOROETHYLENE DERIVATIVE AND USE THEREOF

(71) Applicant: SOOCHOW UNIVERSITY, Suzhou (CN)

(72) Inventors: Dongmei Xu, Suzhou (CN); Wenbo Guo, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 330 days.

(21) Appl. No.: 16/850,379

(22) Filed: Apr. 16, 2020

(65) Prior Publication Data

US 2020/0332105 A1 Oct. 22, 2020

(30) Foreign Application Priority Data

Apr. 19, 2019 (CN) .......................... 201910319981.9

(51) Int. Cl.
*C08L 27/04* (2006.01)
*C07D 491/107* (2006.01)

(52) U.S. Cl.
CPC .......... *C08L 27/04* (2013.01); *C07D 491/107* (2013.01)

(58) Field of Classification Search
CPC ............................ C07D 491/107; C08L 27/04
See application file for complete search history.

(56) References Cited

FOREIGN PATENT DOCUMENTS

| CN | 105859734 | * | 8/2016 |
| CN | 106011217 | * | 10/2016 |

* cited by examiner

*Primary Examiner* — Susanna Moore
(74) *Attorney, Agent, or Firm* — SZDC Law P.C.

(57) ABSTRACT

The present invention relates to the technical field of polymer spectral probes, and particularly to a perchloroethylene derivative and use thereof. The perchloroethylene derivative is prepared by reacting a compound A and a perchloroethylene resin. According to the present invention, the fluorescent polymer can be used as a high-selectivity and high-sensitivity enhanced colorimetric and fluorescent polymer probe for $Fe^{3+}$ and $Cr^{3+}$ As compared with the organic small molecule spectral probe, the polymer spectral probe has improved mechanical property, film forming property and excellent recyclability, and thus has a strong practicability.

8 Claims, 10 Drawing Sheets

PERCHLOROETHYLENE DERIVATIVE AND USE THEREOF

This application claims priority to Chinese Patent Application No.: 201910319981.9, filed on Apr. 19, 2019, which is incorporated by reference for all purposes as if fully set forth herein.

FIELD OF THE INVENTION

The present invention relates to the technical field of spectral probes, and particularly to a perchloroethylene derivative and use thereof. The perchloroethylene derivative can be used as an enhanced $Fe^{3+}$ and $Cr^{3+}$ spectral probe.

DESCRIPTION OF THE RELATED ART

A perchloroethylene resin is a chlorinated product of polyvinyl chloride. The perchloroethylene resin has good weatherability, cold resistance, moisture resistance, chemical corrosion resistance, flame retardance, electric insulativity, mildew resistance and shock resistance. The perchloroethylene can be used for preparing coatings, adhesives and putty, and can also be used for manufacturing petrochemical pipelines, electric wire and cable sleeves, and other products. A rhodamine derivative is a fluorescent dye having a pyran-type xanthene structure, and is usually used as a spectral probe for detecting metal ions (e.g., $Cu^{2+}$, $Hg^{2+}$, $Zn^{2+}$, $Fe^{3+}$, $Pb^{2+}$, $Cr^{3+}$, etc.), anions (e.g., $CN^-$, $P_2O_7^{4-}$ and $CH_3COO^-$, etc.), changes in pH, enzyme activities, cytochromes, nucleic acids, and phosphates, etc. However, the existing small molecular spectral probes have deficiencies in film-forming property and recyclability, and conjugated polymer spectral probes and macromolecular spectral probes obtained by polymerization of fluorescent monomers have deficiencies in economy and practicability.

SUMMARY OF THE INVENTION

In the present invention, a perchloroethylene derivative is obtained through a reaction between chlorine atoms in perchloroethylene and a primary amino group in a condensation product of rhodamine B and aminoethyl sulfide, changes of a target object in an environment or in an organism are reflected by changes in ultraviolet-visible absorption and fluorescence spectra of the perchloroethylene derivative, and the perchloroethylene derivative has the characteristics of a good light stability, large absorption and emission wavelength. As compared with a small-molecule fluorescent probe, the polymer spectral probe has the characteristics of strong film forming capability, good reusability and the like. The perchloroethylene derivative can be used as an enhanced $Fe^{3+}$ and $Cr^{3+}$ spectral probe.

The present invention adopts the following technical solution:

a perchloroethylene derivative of the following chemical formula:

The present invention discloses a method for preparing the above perchloroethylene derivative, which includes the step of reacting compound A and a perchloroethylene resin which are used as raw materials, to obtain the perchloroethylene derivative.

The perchloroethylene resin of the present invention is a commercially available product; and preferably, the perchloroethylene resin has a chlorine content of 61 wt %-68 wt % and a viscosity of 14-28 seconds, and is tested by employing a TU-4 cup (a 20% xylene solution, 25° C.).

The present invention also discloses a method for detecting ions in a solution, which includes the following steps:

(1) preparing a perchloroethylene derivative by reacting a compound A and a perchloroethylene resin, which are used as raw materials; formulating a perchloroethylene derivative solution, and determining the ultraviolet-visible absorption spectrum or fluorescence spectrum of the solution as an initial spectrum;

(2) adding a solution of ions to be detected into the perchloroethylene derivative solution to obtain a mixed solution, and determining the ultraviolet-visible absorption spectrum or fluorescence spectrum of the mixed solution as a detected spectrum; and (3) comparing the detected spectrum with the initial spectrum to complete the detection of the ions in the solution;

wherein, the ions are $Cr^{3+}$ and/or $Fe^{3+}$.

In the aforementioned technical solution, the mass ratio of the perchloroethylene resin to the compound A is 1:(1.87-3.75). The reaction temperature is 60-80° C., and the reaction time is 15-24 h.

In the aforementioned technical solution, the reaction is carried out in 1,2-dichloroethane, dichloromethane or tetrahydrofuran.

In the aforementioned technical solution, the solvents in the perchloroethylene derivative solution are DMF and $H_2O$, preferably the volume ratio of the DMF to $H_2O$ is (1-99):(99-1), and further preferably the volume ratio of the DMF to $H_2O$ is 1:99.

In the present invention, the chemical formula of the compound A is as follows:

In the present invention, the method for preparing the compound A includes the step of reacting rhodamine B and aminoethyl sulfide in dichloromethane to prepare the compound A.

In the aforementioned technical solution, the molar ratio of the rhodamine B to aminoethyl sulfide is 1:5; and the reaction temperature is about 40° C., and the reaction time is 24 h.

Figure 1:
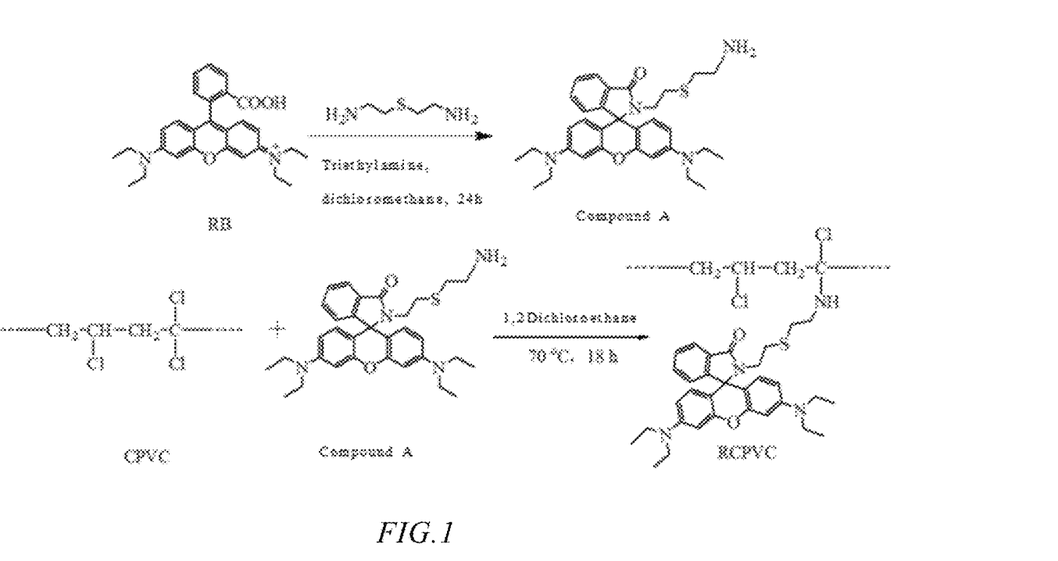
FIG. 1 is a synthetic route of the present invention.

The synthetic route of the present invention is as shown in FIG. 1. In the present invention, dashed lines at both ends of the chemical structural formula of the compound represent repeating units, which is a conventional structural formula representation method in the art.

The synthesis method of the present invention can be specifically exemplified as follows.

Synthesis of the Compound A:

The compound A is synthesized by using the rhodamine B and the aminoethyl sulfide as raw materials, wherein the molar ratio of the rhodamine B to the aminoethyl sulfide is 1:5. By using dichloromethane as the solvent, the rhodamine B and the aminoethyl sulfide are added into dichloromethane in a molar ratio of 1:5 under nitrogen protection, and then triethylamine is added, refluxed, stirred and reacted for 24 h under nitrogen protection. The reaction is ended, and washed with water for 3 times. The organic layer is collected, subjected to rotary evaporation to remove dichloromethane, separated by column chromatography with the eluting agent of methanol/chloroform/petroleum ether (1/10/2, v/v/v), and dried under vacuum to obtain the compound A as yellow solid powder, with the yield of 44.5%.

Synthesis of the Perchloroethylene Derivative (RCPVC):

The mass ratio of the perchloroethylene resin to the compound A is 1:(1.87-3.75). By using 1,2-dichloroethane as the solvent, under nitrogen protection, the perchloroethylene resin and the compound A are reacted under stirring at 70° C. for 15-24 h. After the reaction is ended, the solvent is removed, and the product is washed with ethanol for 3-4 times, and dried in a vacuum drying oven to obtain the RCPVC as a pale yellow solid, with the conversion rate of 40.2%-58.1%.

The present invention also discloses use of the perchloroethylene derivative as the $Cr^{3+}$ and/or $Fe^{3+}$ colorimetric and fluorescent probe.

The present invention further discloses use of the compound A in preparation of the aforementioned perchloroethylene derivative.

As compared with the prior art, the present invention has the following positive effects and advantages:

The present invention utilizes a commercialized perchloroethylene resin to react with the rhodamine derivative to obtain a perchloroethylene derivative, which can integrate the characteristics of good chemical corrosion resistance, flame retardance, electric insulativity, mildew resistance, shock resistance and strong film forming capability of the perchloroethylene resin and the characteristics of long absorption and emission wavelength, sensitive spectral changes of the rhodamine derivative, and detect $Fe^{3+}$ and $Cr^{3+}$ through the increase in the absorbance and fluorescence intensity of the perchloroethylene derivative and the changes of color under natural light and fluorescence color of the perchloroethylene derivative. It is superior to the small-molecular spectral probe in mechanical properties, film-forming property and recyclability, and is superior to the conjugated polymer spectral probes and macromolecular spectral probes obtained by polymerization of fluorescent monomers in economy and practicability.

DETAILED DESCRIPTION OF THE PREFERRED EMBODIMENTS

The perchloroethylene resin of the examples of the present invention has a chlorine content of 61 wt %-68 wt % and a viscosity of 14-28 seconds, and is tested by employing a TU-4 cup (a 20% xylene solution, 25° C.).

Example 1: Synthesis of Compound A

Rhodamine B and aminoethyl sulfide were added into dichloromethane in a molar ratio of 1:5 under nitrogen protection, added with triethylamine, and then refluxed, stirred and reacted for 24 h under nitrogen protection. The reaction was ended, and the resulting product was washed with water for 3 times. The organic layer was collected, subjected to rotary evaporation to remove dichloromethane, separated by column chromatography with the eluting agent of methanol/chloroform/petroleum ether (1/10/2, v/v/v), and dried under vacuum to obtain a compound A as yellow solid powder, with the yield of 44.5%.

Figure 2:
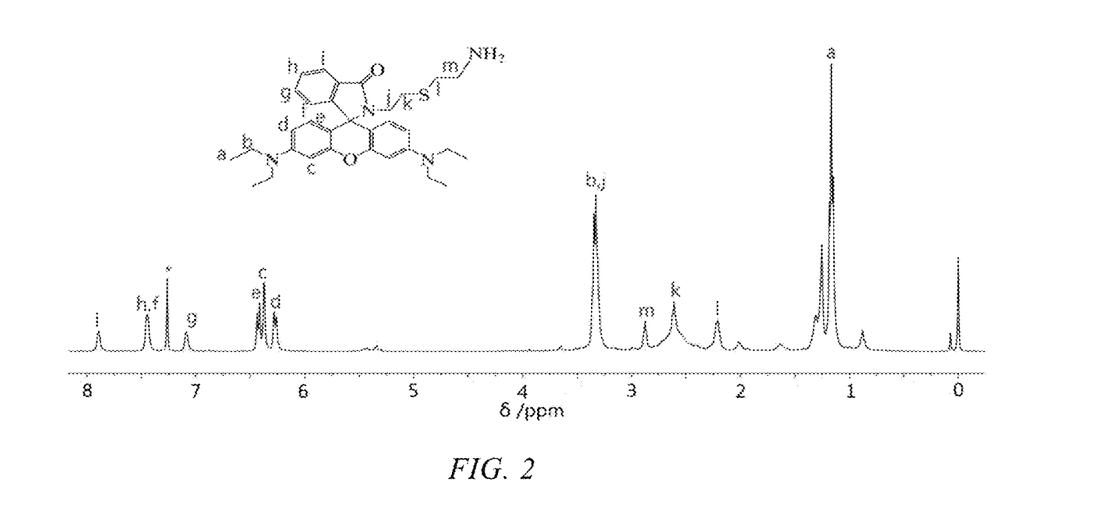
FIG. 2 is a nuclear magnetic resonance hydrogen spectrogram of the compound A ($CDCl_3$, 400 MHz)

FIG. 2 is a nuclear magnetic resonance hydrogen spectrogram of the compound A ($CDC_3$, 400 MHz): $^1$H NMR (400 MHz, $CDCl_3$, δ/ppm): 7.89 (s, 1H, PhH), 7.49 (m, 2H, PhH), 7.05 (d, J=8.4 Hz, 1H, PhH), 6.43 (d, J=8.7 Hz, 2H, PhH), 6.37 (s, 2H, PhH), 6.27 (d, J=8.3 Hz, 2H, PhH), 3.42-3.21 (m, 10H, $CH_3CH_2N$ and $SCH_2CH_2N$), 2.99-2.76 (m, 2H, $SCH_2CH_2NH_2$), 2.64-2.58 (t, J=6.4 Hz, 2H, $SCH_2CH_2N$), 2.26-2.15 (t, J=8.0 Hz, 2H, $SCH_2CH_2NH_2$), 1.21-1.10 (t, J=6.7 Hz, 12H, $CH_3CH_2N$).

Example 2: Preparation of Perchloroethylene Derivative (RCPVC)

Using 1,2-dichloroethane as the solvent, the perchloroethylene and the compound A in a mass ratio of 1:2.52, as raw materials, were reacted with stirring under the protection of $N_2$ at the temperature of 70° C. for 18 h; and then the reaction was ended, the solvent was removed, and the product was washed with ethanol for 3 times, and dried in a vacuum drying oven to obtain the RCPVC as a pale yellow solid with the conversion rate of 58.1%, which was used for the following tests.

Figure 3:
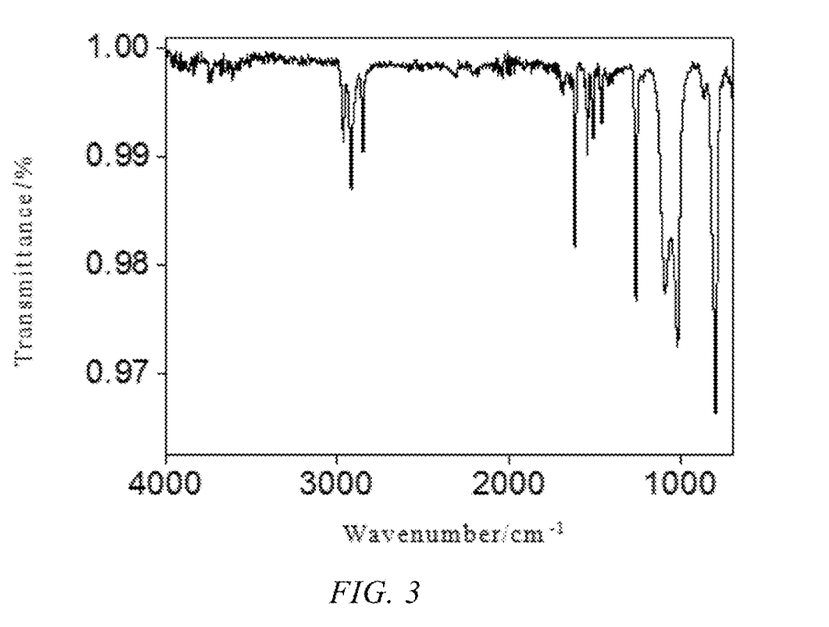
FIG. 3 is an infrared spectrogram of the RCPVC.

FIG. 3 is an infrared spectrogram of the RCPVC:IR (KBr) cm$^{-1}$:3600 (—N—H), 2964 (Ar—H), 2916, 2848 (—$CH_3$, —$CH_2$), 1616 (C=O), 1542, 1508, 1458 (Ar—H), 1261 (C—N), 1091, 1020 (—C—S—C—), 796 (C—Cl).

Figure 4:
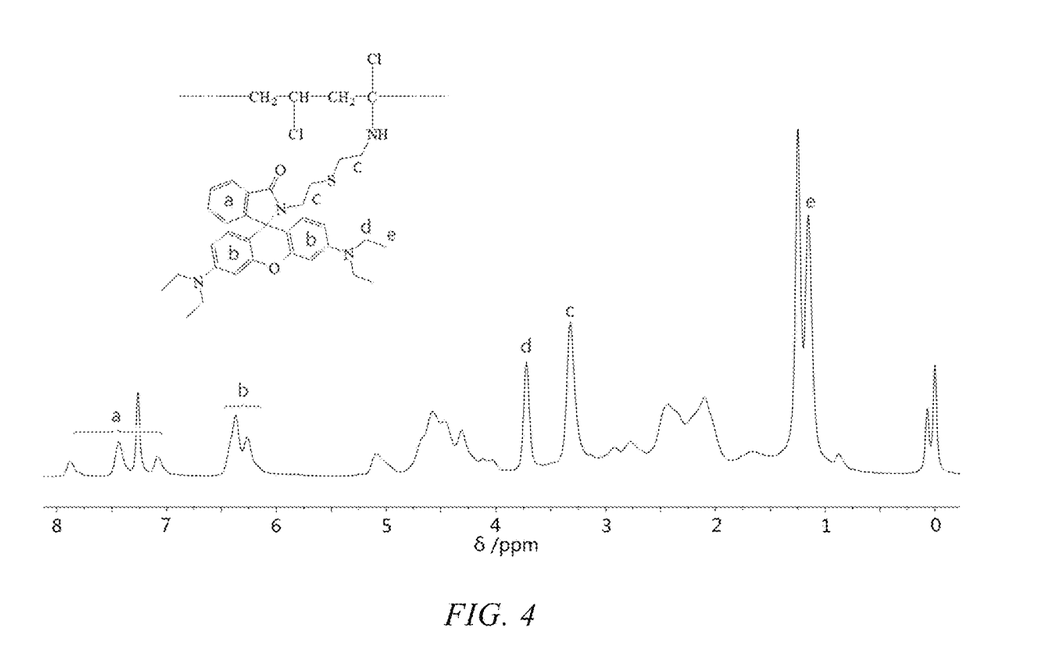
FIG. 4 is a nuclear magnetic resonance hydrogen spectrogram of the RCPVC ($CDCl_3$, 400 MHz)

FIG. 4 is a nuclear magnetic resonance hydrogen spectrogram of the RCPVC ($CDC_3$, 400 MHz): $^1$H NMR ($CDCl_3$, 400 MHz): δ ppm 7.96-6.96 (m, Ar—H in the compound A), 6.55-6.05 (m, Ar—H in the compound A), 3.72 (m, $CH_3CH_2NCH_2CH_3$ in the compound A), 3.32 (m, $SCH_2CH_2N$ in the compound A), 2.63-1.47 (m, CH, $CH_2$ and $CH_3$ other than those listed separately), 1.47-0.47 (t, J=6.8, $CH_3CH_2NCH_2CH_3$ in the compound A).

Using 1,2-dichloroethane as the solvent, the perchloroethylene and the compound A in a mass ratio of 1:1.87, were reacted with stirring under the protection of $N_2$ at the temperature of 70° C. for 18 h. The reaction was ended, the solvent was removed, and the product was washed with ethanol for 3 times, and dried in a vacuum drying oven to obtain the RCPVC as a pale yellow solid with the conversion rate of 49.6%.

Using 1,2-dichloroethane as the solvent, the perchloroethylene and the compound A in a mass ratio of 1:3.75, were reacted with stirring under the protection of $N_2$ at the temperature of 70° C. for 18 h. The reaction was ended, the solvent was removed, and the product was washed with ethanol for 3 times, and dried in a vacuum drying oven to obtain the RCPVC as a pale yellow solid with the conversion rate of 46.1%.

Figure 5:
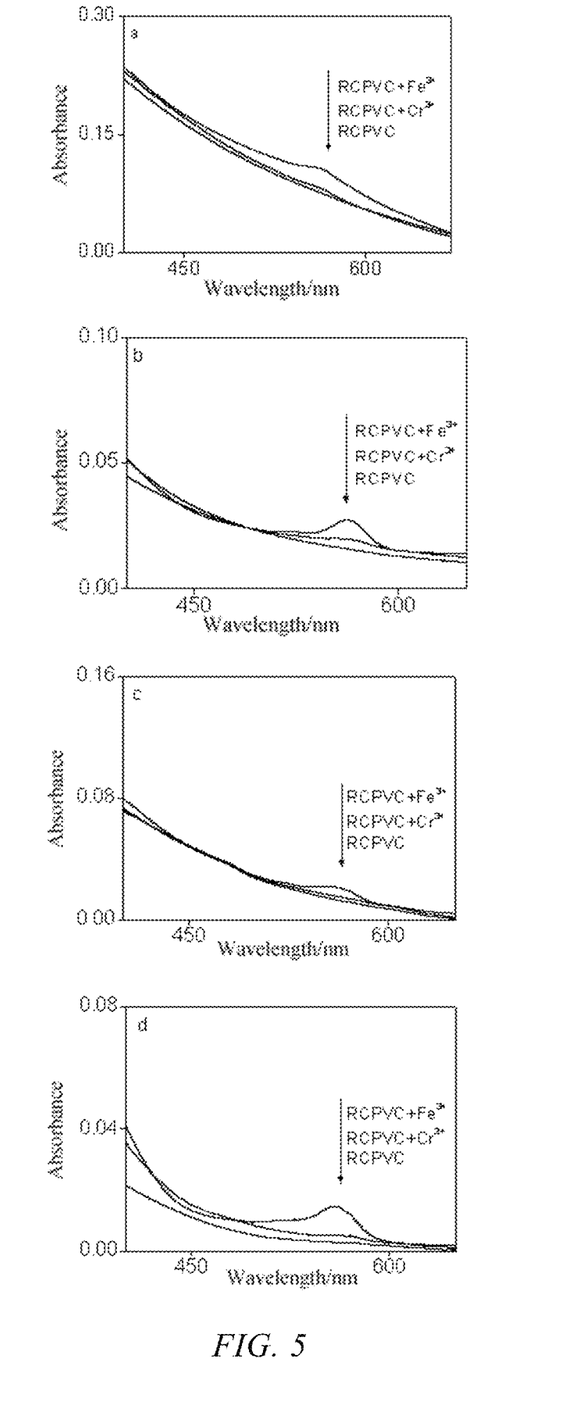
FIG. 5 is a graph showing the response of the ultraviolet-visible absorption spectrum of the RCPVC to $Fe^{3+}$ and $Cr^{3+}$.

Example 3: Response of Ultraviolet-Visible Absorption Spectrum of RCPVC to $Fe^{3+}$ and $Cr^{3+}$ in Different Solvents In solvent systems of DMF and $H_2O$ at different proportions, the same concentration of $Fe^{3+}$ or $Cr^{3+}$ were added into the RCPVC solution, and then the ultraviolet-visible absorption spectra of the RCPVC solution before and after the addition of the ions were tested. The results are shown in FIG. 5. The solvents: DMF and $H_2O$ at the proportions of 1/99, 2/8, 8/2, 99/1 respectively; concentrations: 50 μg/mL (RCPVC), and 50 μM ($Fe^{3+}$ or $Cr^{3+}$); and solvents: a: DMF/$H_2O$ (1/99, v/v); b: DMF/$H_2O$ (2/8, v/v); c: DMF/$H_2O$ (8/2, v/v); d: DMF/$H_2O$ (99/1, v/v). The addition of $Fe^{3+}$ enables obvious changes of the ultraviolet-visible absorption spectrum of the RCPVC, such that the absorbances at 562 nm are increased by 2.63 times, 1.94 times, 1.80 times and 1.31 times respectively. The addition of $Cr^{3+}$ enables that the absorbances of the RCPVC at 562 nm are increased by 1.62 times, 1.40 times, 1.23 times and 1.14 times respectively.

Figure 6:
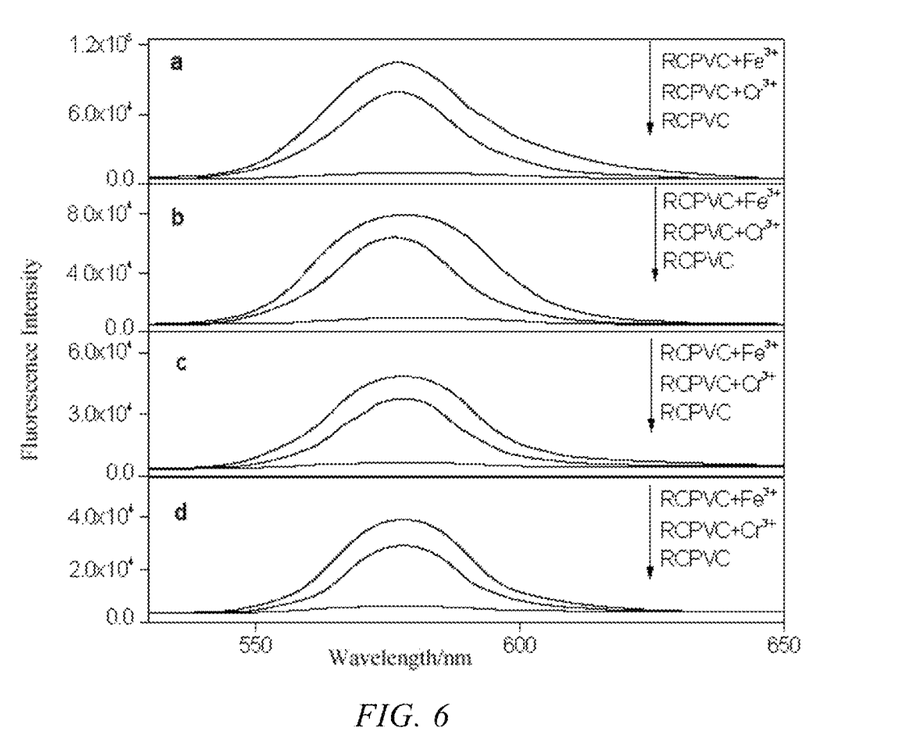
FIG. 6 is a graph showing the response of the fluorescence spectrum of the RCPVC to $Fe^{3+}$ and $Cr^{3+}$.

Example 4: Response of Fluorescence Spectrum of RCPVC to $Fe^{3+}$ and $Cr^{3+}$ in Different Solvents In solvent systems of DMF and $H_2O$ at different proportions, the same concentration of $Fe^{3+}$ or $Cr^{3+}$ were added into the RCPVC solution, and then the fluorescence spectra of the RCPVC solution before and after the addition of the ions were tested. The results are shown in FIG. 6. The solvents: DMF and $H_2O$ at the proportions of 1/99, 2/8, 8/2, 99/1, respectively; concentrations: 50 μg/mL (RCPVC), 50 μM ($Fe^{3+}$ or $Cr^{3+}$); excitation wavelength: 467 nm, slit width: 5 nm; and solvents: a: DMF/$H_2O$ (1/99, v/v); b: DMF/$H_2O$ (2/8, v/v); c: DMF/$H_2O$ (8/2, v/v); d: DMF/$H_2O$ (99/1, v/v). The addition of $Fe^{3+}$ enables that the fluorescence intensities at 578 nm are increased by 11.58 times, 8.42 times, 7.26 times and 6.62 times respectively; and the addition of $Cr^{3+}$ enables that the corresponding fluorescence intensities of the RCPVC are increased by 8.75 times, 6.76 times, 5.61 times and 4.92 times respectively.

Figure 7:
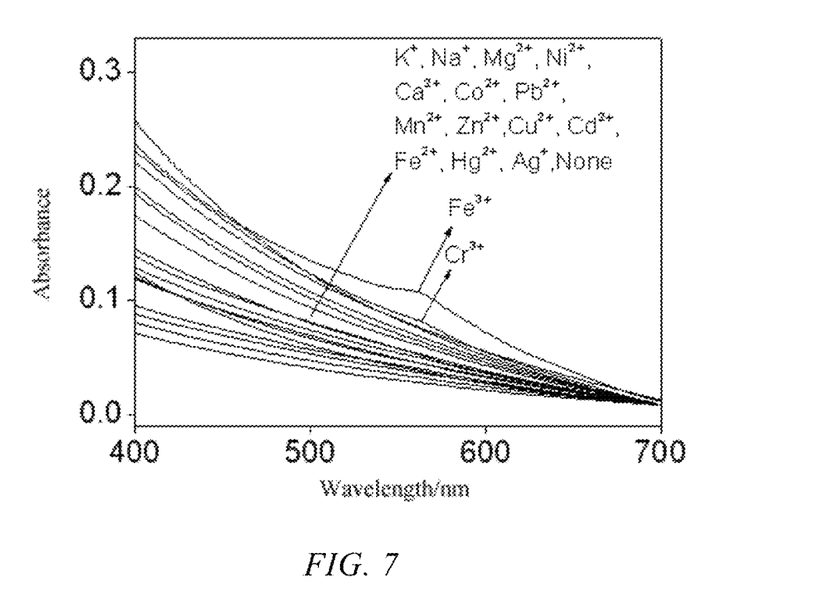
FIG. 7 is a graph showing the response of the ultraviolet-visible absorption spectrum of the RCPVC to different metal ions.

Example 5: Selectivity and Sensitivity of Ultraviolet-Visible Absorption Spectrum of RCPVC to $Fe^{3+}$ and $Cr^{3+}$ Since both the spectral changes of the RCPVC caused by $Fe^{3+}$ and $Cr^{3+}$ were the largest in the DMF/$H_2O$ (1/99, v/v) system, subsequent researches were carried out in this system. In the DMF/$H_2O$ (1/99, v/v) system, $K^+$, $Na^+$, $Mg^{2+}$, $Cu^{2+}$, $Zn^{2+}$, $Cr^{3+}$, $Fe^{2+}$, $Ca^{2+}$, $Pb^{2+}$, $Hg^{2+}$, $Ni^{2+}$, $Mn^{2+}$, $Co^{2+}$, $Cd^{2+}$, $Ag^+$ and $Fe^{3+}$ were respectively added into the RCPVC solution, and then the ultraviolet-visible absorption spectra of the RCPVC solutions before and after the addition of the ions were determined. The results are shown in FIG. 7. The solvents: DMF/$H_2O$ (1/99, v/v), and concentrations: 50 μg/mL (RCPVC), 50 μM (metal ions). From the following figure, it could be observed that a new obvious absorption peak occurs at 562 nm in the ultraviolet-visible absorption spectrum of the RCPVC solution added with $Fe^{3+}$, and the absorbance is increased by 2.63 times, and the color of the solution changes from yellow to pink. The addition of $Cr^{3+}$ also causes that a weak absorption peak occurs at 562 nm in the ultraviolet-visible absorption spectrum of the RCPVC solution, and the absorbance at 562 nm is increased by 1.62 times, while the addition of other ions has little effect on the ultraviolet-visible absorption spectrum of the RCPVC solution. This indicates that the RCPVC could be used for colorimetric detection of $Fe^{3+}$ and $Cr^{3+}$ in the DMF/$H_2O$ (1/99, v/v) system.

Figure 8:
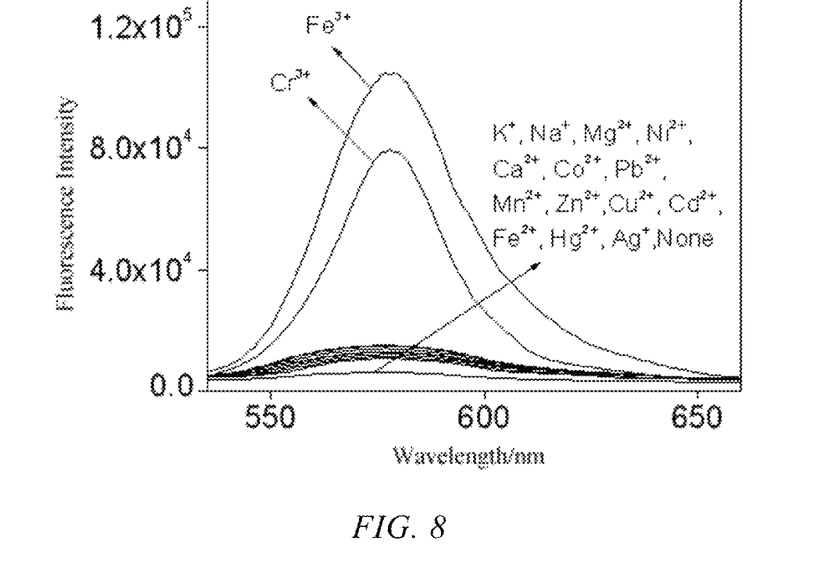
FIG. 8 is a graph showing the response of the fluorescence spectrum of the RCPVC to different metal ions.

Example 6: Selectivity and Sensitivity of Fluorescence Spectrum of RCPVC to $Fe^{3+}$ and $Cr^{3+}$ In the DMF/$H_2O$ (1/99, v/v) system, $K^+$, $Na^+$, $Mg^{2+}$, $Cu^{2+}$, $Zn^{2+}$, $Cr^{3+}$, $Fe^{2+}$, $Ca^{2+}$, $Pb^{2+}$, $Hg^{2+}$, $Ni^{2+}$, $Mn^{2+}$, $Co^{2+}$, $Cd^{2+}$, $Ag^+$ and $Fe^{3+}$ were respectively added into the RCPVC solutions, and then the fluorescence spectra of the RCPVC solutions before and after the addition of the ions were determined. The results are shown in FIG. 8. The solvents: $DMF/H_2O$ (1/99, v/v), concentrations: 50 µg/mL (RCPVC), 50 µM (metal ions); excitation wavelength: 467 nm, and slit width: 5 nm. From FIG. 8 it could be observed that, the addition of $Fe^{3+}$ enables that the fluorescence intensity at 578 nm in the fluorescence spectrum of the RCPVC is increased by 11.58 times; and the addition of $Cr^{3+}$ enables that the fluorescence intensity at 578 nm is increased by 8.75 times, while other ions had little effect on the fluorescence spectrum of the RCPVC. This indicates that the RCPVC could be used as a fluorescent probe for $Fe^{3+}$ and $Cr^{3+}$ in the $DMF/H_2O$ (1/99, v/v) system.

Figure 9:
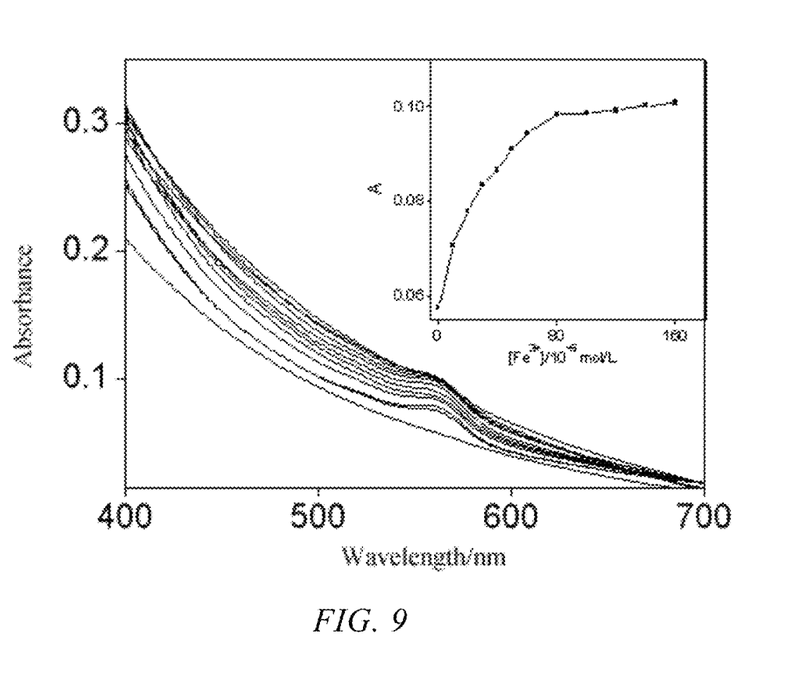
FIG. 9 is a graph showing the relationship between the ultraviolet-visible absorption spectrum of the RCPVC and the concentration of $Fe^{3+}$.

Example 7: Relationship Between Ultraviolet-Visible Absorption Spectrum of RCPVC and Concentration of $Fe^{3+}$ In the $DMF/H_2O$ (1/99, v/v) system, different concentrations of $Fe^{3+}$ were respectively added into the RCPVC solutions, and the ultraviolet-visible absorption spectra of the RCPVC solutions were determined. The results are shown in FIG. 9. The solvents: $DMF/H_2O$ (1/99, v/v); concentrations: 50 µg/mL (CPVCR), and the concentrations of $Fe^{3+}$ from top to bottom were sequentially 0, 10, 20, 30, 40, 50, 60, 80, 100, 120, 140, and 160 µM. The inset shows the relationship between the absorbance at 562 nm and the concentration of $Fe^{3+}$. It could be observed from the figure that, with the increase of the concentration of $Fe^{3+}$, the absorbance at 562 nm is also increased accordingly, and the absorbance of the RCPVC would not increase any more when the concentration of $Fe^{3+}$ reaches 80 µM. When the concentration of $Fe^{3+}$ is between 0-60 µM, the absorbance at 562 nm shows a good linear relationship with the concentration of $Fe^{3+}$, and its linear equation is $A=0.0005933 \times [Fe^{3+}]+0.06282$, and the correlation coefficient R=0.929. At this time the detection limit for $Fe^{3+}$ is $1.58 \times 10^{-6}$ M, indicating that the RCPVC could quantitatively detect $Fe^{3+}$ through a colorimetric method.

Figure 10:
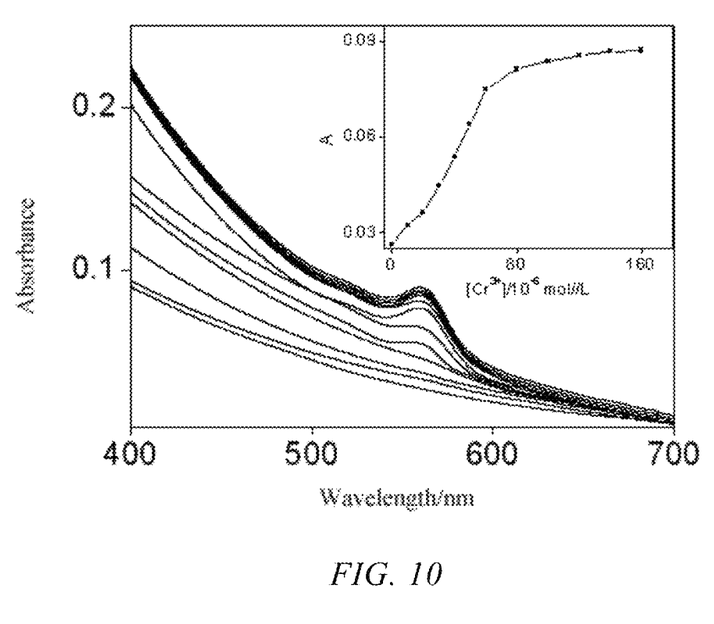
FIG. 10 is a graph showing the relationship between the ultraviolet-visible absorption spectrum of the RCPVC and the concentration of $Cr^{3+}$.

Example 8: Relationship Between Ultraviolet-Visible Absorption Spectrum of RCPVC and Concentration of $Cr^{3+}$ In the $DMF/H_2O$ (1/99, v/v) system, different concentrations of $Cr^{3+}$ were respectively added into the RCPVC solutions, and the ultraviolet-visible absorption spectra of the RCPVC solutions were determined. The results are shown in FIG. 10. The solvents: $DMF/H_2O$ (1/99, v/v); concentrations: 50 µg/mL (CPVCR), and the concentrations of $Cr^{3+}$ from top to bottom were sequentially 0, 10, 20, 30, 40, 50, 60, 80, 100, 120, 140, and 160 µM. The inset shows the relationship between the absorbance at 562 nm and the concentration of $Cr^3$. It could be observed from FIG. 10 that, with the increase of the concentration of $Cr^{3+}$, the absorbance at 562 nm is also increased accordingly, and the absorbance of the RCPVC would not increase any more when the concentration of $Cr^{3+}$ reaches 80 µM. When the concentration of $Cr^{3+}$ is between 0-80 µM, the absorbance at 562 nm shows a good linear relationship with the concentration of $Cr^{3+}$, and its linear equation is $A=0.0007478 \times [Cr^{3+}]+0.02462$, and the correlation coefficient R=0.974. At this time the detection limit for $Cr^{3+}$ is $2.47 \times 10^{-6}$ M, indicating that the RCPVC could quantitatively detect $Cr^{3+}$ through a colorimetric method.

Figure 11:
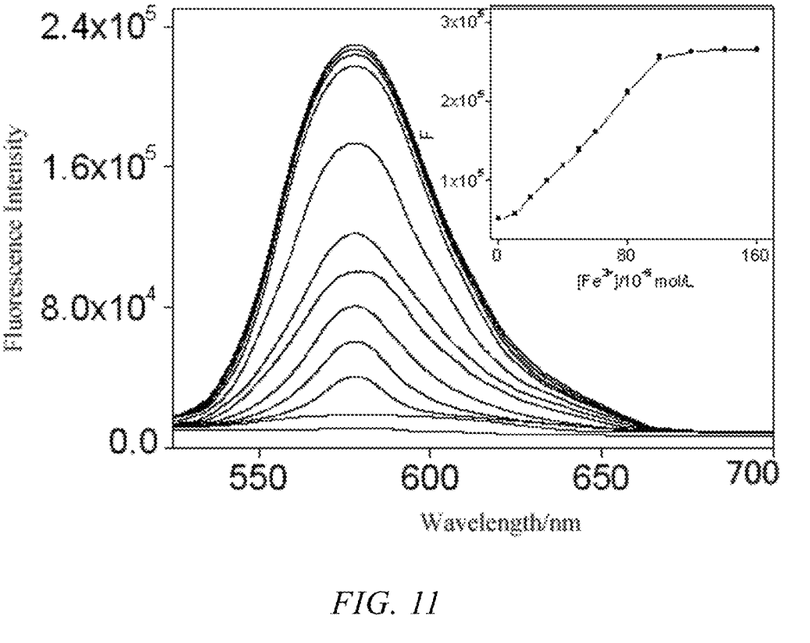
FIG. 11 is a graph showing the relationship between the fluorescence spectrum of the RCPVC and the concentration of $Fe^{3+}$.

Example 9: Relationship Between Fluorescence Spectrum of RCPVC and Concentration of $Fe^{3+}$ In the $DMF/H_2O$ (1/99, v/v) system, different concentrations of $Fe^{3+}$ were respectively added into the RCPVC solutions, and the fluorescence spectra of the RCPVC solutions were determined. The results are shown in FIG. 11. The solvents: $DMF/H_2O$ (1/99, v/v); concentrations: 50 µg/mL (CPVCR), and the concentrations of $Fe^{3+}$ from top to bottom were sequentially 0, 10, 20, 30, 40, 50, 60, 80, 100, 120, 140, 160 µM; excitation wavelength: 467 nm, and slit width: 5 nm. The inset shows the relationship between fluorescence intensity at 578 nm and the concentration of $Fe^{3+}$. It could be observed from FIG. 11 that, with the increase of the concentration of $Fe^{3+}$, the fluorescence intensity at 578 nm is also increased accordingly, and the fluorescence intensity of the RCPVC would not increase any more when the concentration of $Fe^{3+}$ reaches 100 µM. When the concentration of $Fe^{3+}$ is between 0-100 µM, the fluorescence intensity at 578 nm shows a good linear relationship with the concentration of $Fe^{3+}$, and its linear equation is $F=2111.924 \times [Fe^{3+}]+38492.531$, and the correlation coefficient R=0.991. At this time the detection limit for $Fe^{3+}$ is $7.22 \times 10^{-6}$ M, indicating that the RCPVC could quantitatively detect $Fe^{3+}$ through a fluorescence method.

Figure 12:
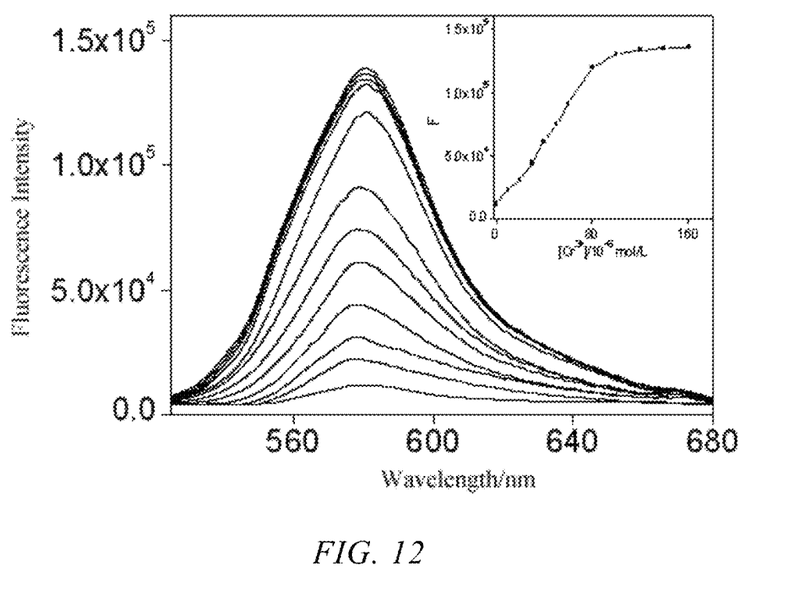
FIG. 12 is a graph showing the relationship between the fluorescence spectrum of the RCPVC and the concentration of $Cr^{3+}$.

Example 10: Relationship Between Fluorescence Spectrum of RCPVC and Concentration of $Cr^{3+}$ In the $DMF/H_2O$ (1/99, v/v) system, different concentrations of $Cr^{3+}$ were respectively added into the RCPVC solutions, and the fluorescence spectra of the RCPVC solution were determined. The results are shown in FIG. 12. The solvents: $DMF/H_2O$ (1/99, v/v); concentrations: 50 µg/mL (CPVCR), and the concentrations of $Cr^{3+}$ from top to bottom were sequentially 0, 10, 20, 30, 40, 50, 60, 80, 100, 120, 140, 160 µM; excitation wavelength: 467 nm, and slit width: 5 nm. The inset shows the relationship between fluorescence intensity at 578 nm and the concentration of $Cr^{3+}$. It could be observed from FIG. 11 that, with the increase of the concentration of $Cr^{3+}$, the fluorescence intensity at 578 nm is also increased accordingly, and the fluorescence intensity of the RCPVC would not increase any more when the concentration of $Cr^{3+}$ reaches 100 µM. When the concentration of $Cr^{3+}$ is between 0-100 µM, the fluorescence intensity at 578 nm shows a good linear relationship with the concentration of $Cr^{3+}$, and its linear equation is $F=1274.051 \times [Cr^{3+}]+9873.322$, and the correlation coefficient R=0.986. At this time the detection limit for $Cr^{3+}$ is $1.20 \times 10^{-6}$ M, indicating that the RCPVC could quantitatively detect $Cr^{3+}$ through a fluorescence method.

Figure 13:
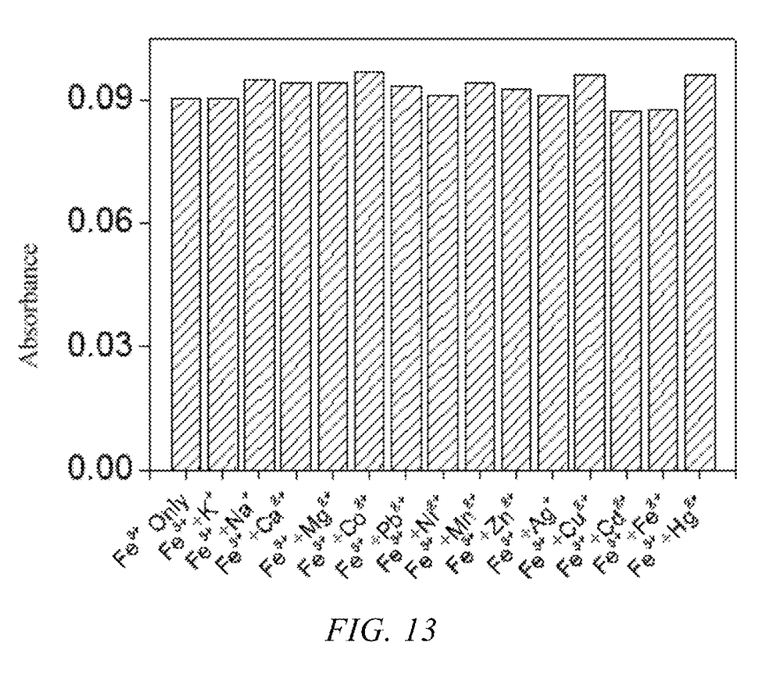
FIG. 13 is a graph showing the influence of co-existing ions on the RCPVC colorimetric detection of $Fe^{3+}$.

Example 11: Effect of Co-Existing Ions on RCPVC Colorimetric Detection of $Fe^{3+}$ In the $DMF/H_2O$ (1/99, v/v) system, other common metal ions were added into the RCPVC-$Fe^{3+}$ solutions, and then the ultraviolet-visible absorption spectra were determined, so as to investigate the anti-interference condition when the RCPVC was used for detecting $Fe^{3+}$ by the absorbance at 562 nm. The results are shown in FIG. 13. The solvents: $DMF/H_2O$ (1/99, v/v), and concentration: 50 µg/mL (RCPVC). The addition of 20 µM of $Hg^{2+}$, $Mg^{2+}$, $Pb^{2+}$, $Ni^{2+}$, $Cd^{2+}$, $Fe^{2+}$ and 50 µM of $K^+$, $Na^+$, $Ca^{2+}$, $Cu^{2+}$, $Zn^{2+}$, $Mn^{2+}$, $Co^{2+}$ and $Ag^+$ has little effect on the ultraviolet-visible absorption spectrum of the RCPVC-$Fe^{3+}$ solution. The aforementioned results show that the RCPVC has a strong anti-interference capability when used for detecting $Fe^{3+}$ by a colorimetric method.

Figure 14:
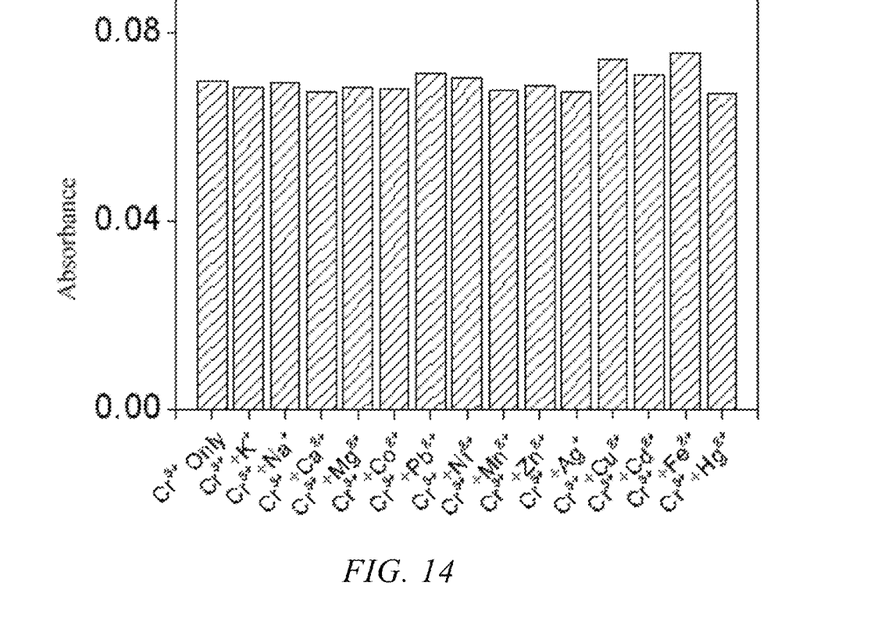
FIG. 14 is a graph showing the influence of co-existing ions on the RCPVC colorimetric detection of $Cr^{3+}$.

Example 12: Effect of Co-Existing Ions on RCPVC Colorimetric Detection of $Cr^{3+}$ In the DMF/$H_2O$ (1/99, v/v) system, other common metal ions were added into the RCPVC-$Cr^{3+}$ solutions, and then the ultraviolet-visible absorption spectra were determined, so as to observe the anti-interference condition when the RCPVC was used for detecting $Cr^{3+}$ by the absorbance at 562 nm. The results are shown in FIG. 14. The solvents: DMF/$H_2O$ (1/99, v/v), and the concentration: 50 μg/mL (RCPVC). The addition of 20 μM of $Pb^{2+}$, $Ni^{2+}$, $Cu^{2+}$, $Fe^{2+}$, and 50 μM of $K^+$, $Na^+$, $Mg^{2+}$, $Ca^{2+}$, $Zn^{2+}$, $Hg^{2+}$, $Mn^{2+}$, $Co^{2+}$, $Cd^{2+}$ and $Ag^+$ has little effect on the ultraviolet-visible absorption spectrum of the RCPVC-$Cr^{3+}$ solution. The aforementioned results show that the RCPVC has a strong anti-interference capability when used for detecting $Cr^{3+}$ by a colorimetric method.

Figure 15:
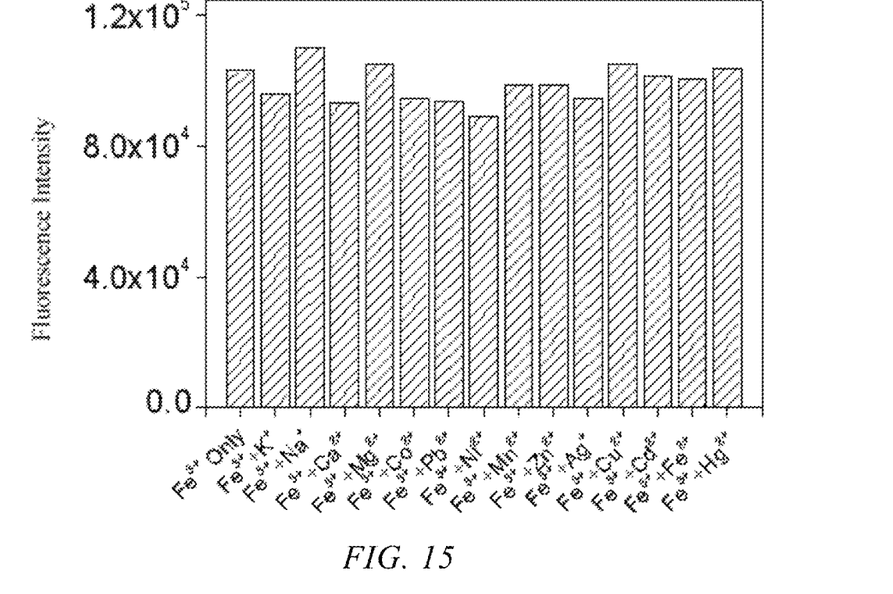
FIG. 15 is a graph showing the influence of co-existing ions on the RCPVC fluorescence detection of $Fe^{3+}$.

Example 13: Influence of Co-Existing Ions on RCPVC Fluorescence Detection of $Fe^{3+}$ In the DMF/$H_2O$ (1/99, v/v) system, other common metal ions were added into the RCPVC-$Fe^{3+}$ solutions, and then the fluorescence spectra were determined, so as to investigate the anti-interference condition when the RCPVC was used for detecting $Fe^{3+}$ by observing the fluorescence intensity at 578 nm. The results are shown in FIG. 15. The solvents: DMF/$H_2O$ (1/99, v/v), and concentration: 50 μg/mL (RCPVC). The addition of 20 μM of $Hg^{2+}$, $Mg^{2+}$, $Pb^{2+}$, $Ni^{2+}$, $Cd^{2+}$, $Fe^{2+}$ and 50 μM of $K^+$, $Na^+$, $Ca^{2+}$, $Cu^{2+}$, $Zn^{2+}$, $Mn^{2+}$, $Co^{2+}$ and $Ag^+$ has little effect on the fluorescence spectrum of the RCPVC-$Fe^{3+}$ solution. The aforementioned results show that the RCPVC has a strong anti-interference capability when used for detecting $Fe^{3+}$ by a fluorescence method.

Figure 16:
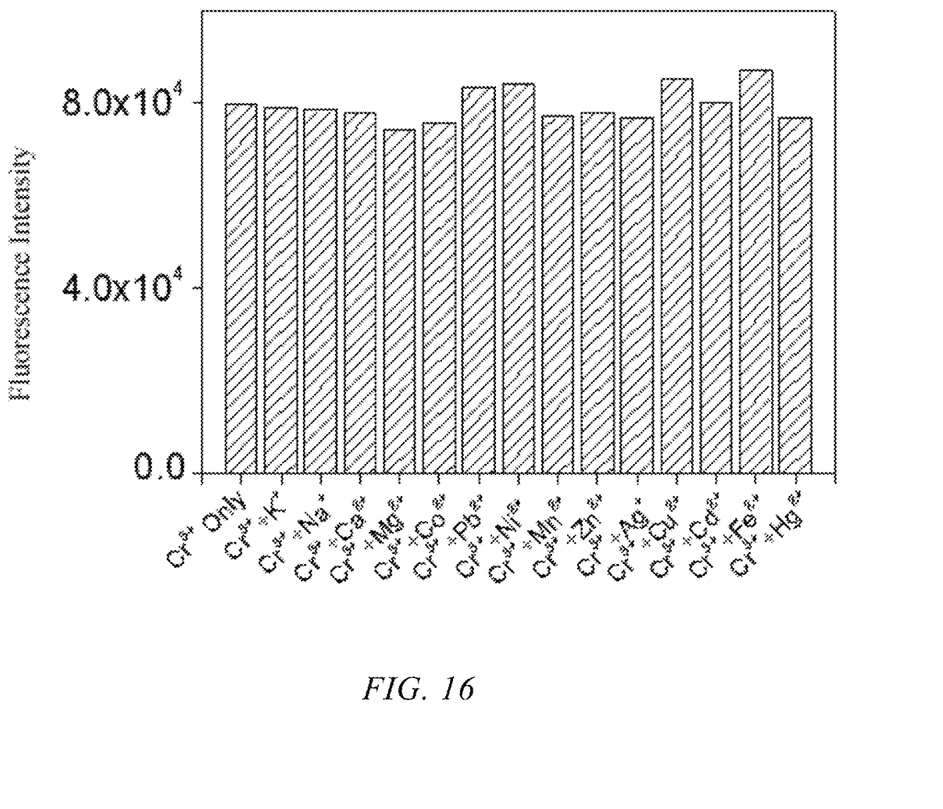
FIG. 16 is a graph showing the influence of co-existing ions on the RCPVC fluorescence detection of $Cr^{3+}$.

Example 14: Influence of Co-Existing Ions on RCPVC Fluorescence Detection of $Cr^{3+}$ In the DMF/$H_2O$ (1/99, v/v) system, other common metal ions were added into the RCPVC-$Cr^{3+}$ solutions, and then the fluorescence spectra were determined, so as to observe the anti-interference condition when the RCPVC was used for detecting $Cr^{3+}$ by the fluorescence intensity at 578 nm. The results are shown in FIG. 16. The solvents: DMF/$H_2O$ (1/99, v/v), and the concentration: 50 μg/mL (RCPVC). The addition of 20 μM of $Pb^{2+}$, $Ni^{2+}$, $Cu^{2+}$, $Fe^{2+}$, and 50 μM of $K^+$, $Na^+$, $Mg^{2+}$, $Ca^{2+}$, $Zn^{2+}$, $Hg^{2+}$, $Mn^{2+}$, $Co^{2+}$, $Cd^{2+}$ and $Ag^+$ has little effect on the fluorescence spectrum of the RCPVC-$Cr^{3+}$ solution. The aforementioned results show that the RCPVC has a strong anti-interference capability when used for detecting $Cr^{3+}$ by a fluorescence method.

Example 15: Film-Forming Property and Mechanical Strength of RCPVC

Figure 17:
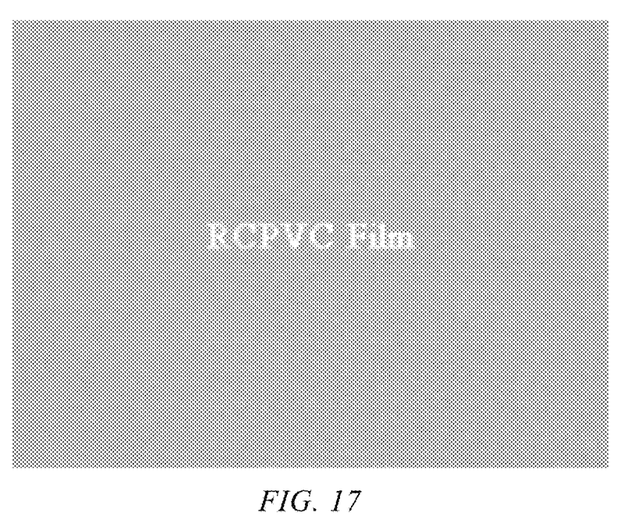
FIG. 17 shows an RCPVC film.

A RCPVC solution with a concentration of 250 μg/mL was formulated with dichloromethane, and evenly coated on a glass slide with a size of 1.5 cm×2.5 cm. After the solvent volatilized completely, a plastic thin film with excellent mechanical strength was formed, as shown in FIG. 17. Moreover, the solution of the small-molecule compound A in dichloromethane ($1\times10^{-3}$ mol/L) was coated on a glass slide of the same size, and the film could not be obtained after the solvent volatilized completely. It could be seen that the film-forming property and mechanical strength of the RCPVC are obviously better than those of the small-molecule compound A.

Example 16: Reusability of RCPVC

Figure 18:
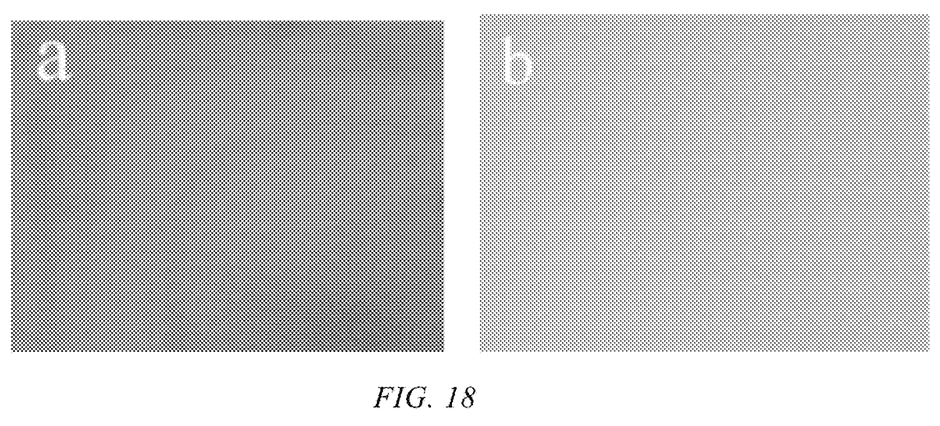
FIG. 18 shows the color of the RCPVC film.

The RCPVC-coated film prepared in Example 15 was soaked in 6 mL of a colorless and transparent hydrochloric acid aqueous solution with a concentration of 0.1 mol/L, and the color of the film became pink after 12 h, as shown in FIG. 18a, which was due to the ring opening of the rhodamine unit in the RCPVC as caused by hydrogen ions in the hydrochloric acid aqueous solution. Then the pink film was soaked in 6 mL of a colorless and transparent NaOH aqueous solution with a concentration of 0.1 mol/L, and the pink color of the film was faded (FIG. 18b), which was due to recovering of a closed ring of the rhodamine unit as caused by hydroxide ions in the NaOH aqueous solution. Therefore, it could be seen that the RCPVC could be reused.

In the present invention, a novel perchloroethylene derivative (RCPVC) is prepared, which can be used as the enhanced $Fe^{3+}$ and $Cr^{3+}$ spectral probe, and opens up a new application field of the perchloroethylene resin.

What is claimed is:

1. A perchloroethylene monomer having a chemical formula of:

2. A method for preparing a perchloroethylene polymer having a chemical formula comprising reacting a compound A with a perchloroethylene resin to obtain the perchloroethylene derivative.

3. The method according to claim 2, wherein a mass ratio of the perchloroethylene resin to the compound A is 1:1:87-3.75 a reaction temperature is 60-80° C., and a reaction time is 15-24 h.

4. The method according to claim 2, wherein the reaction is carried out in 1,2-dichloroethane, dichloromethane or tetrahydrofuran.

5. The method according to claim 2, further comprising reacting rhodamine B with aminoethyl sulfide in dichloromethane to prepare the compound A.

6. The method according to claim 5, wherein a molar ratio of the rhodamine B to aminoethyl sulfide is 1:5, a reaction temperature is a reflux temperature (about 40° C.) of solvent dichloromethane, and a reaction time is 24 hours.

7. A $Cr^{3+}$ and/or $Fe^{3+}$ colorimetric and fluorescent probe comprising the perchloroethylene derivative of claim 1.

8. The $Cr^{3+}$ and/or $Fe^{3+}$ colorimetric and fluorescent probe according to claim 7, wherein the $Cr^{3+}$ and/or $Fe^{3+}$ colorimetric and fluorescent probe is used with DMF and $H_2O$.

* * * * *